US008867811B2

(12) United States Patent
Raju et al.

(10) Patent No.: US 8,867,811 B2
(45) Date of Patent: Oct. 21, 2014

(54) MR IMAGING GUIDED THERAPY

(75) Inventors: Balasundara Raju, Tarrytown, NY (US); Ajay Anand, Fishkill, NY (US); Gosta Jakob Ehnholm, Helsinki (FI)

(73) Assignee: Koninklijke Philips N.V., Eindhoven (NL)

( * ) Notice: Subject to any disclaimer, the term of this patent is extended or adjusted under 35 U.S.C. 154(b) by 419 days.

(21) Appl. No.: 13/321,557

(22) PCT Filed: May 27, 2010

(86) PCT No.: PCT/IB2010/052357
§ 371 (c)(1),
(2), (4) Date: Nov. 21, 2011

(87) PCT Pub. No.: WO2010/140086
PCT Pub. Date: Dec. 9, 2010

(65) Prior Publication Data
US 2012/0070058 A1 Mar. 22, 2012

Related U.S. Application Data

(60) Provisional application No. 61/183,116, filed on Jun. 2, 2009.

(51) Int. Cl.
*G06K 9/00* (2006.01)
*A61B 6/00* (2006.01)
*A61N 7/02* (2006.01)
*A61B 17/00* (2006.01)
*A61B 19/00* (2006.01)

(52) U.S. Cl.
CPC .......... *A61N 7/02* (2013.01); *A61B 2017/00084* (2013.01); *A61B 2019/5236* (2013.01)
USPC ........................... 382/131; 600/411; 600/412

(58) Field of Classification Search
None
See application file for complete search history.

(56) References Cited

U.S. PATENT DOCUMENTS 5,553,618 A * 9/1996 Suzuki et al. ................. 600/411
5,722,411 A * 3/1998 Suzuki et al. ................. 600/439

(Continued)

FOREIGN PATENT DOCUMENTS

WO 03075771 A1 9/2003
WO 2007047247 A1 4/2007
WO 2008152542 A2 12/2008

OTHER PUBLICATIONS

By R. Salomir "Automatic Feedback Control of the Temperature for MRI-Guided Therapeutic Ultrasound"; Engineering in Medicine and Biology Society, 2007. EMBS 2007. 29th Annual International Conference of the IEEE, vol. , Issue , Aug. 22-26, 2007 pp. 222-225. Publ.

(Continued)

Primary Examiner — Wenpeng Chen

(57) ABSTRACT

A therapeutic system, comprising: a MR imaging unit arranged to acquire MR signals from a patient in an examination volume, and a thermal treatment unit for depositing thermal energy within tissue of the patient. The system is arranged for: initiating a thermal treatment by heating the tissue at a focus within the examination volume selectively acquiring MR signals from a first image plane, including the focus, reconstructing a thermographic MR image from the MR signals acquired from the first image plane, computing a baseline thermographic MR image from a temperature distribution within at least one second image plane, moving the focus to a new position within the examination volume, changing the position and/or orientation of the first image plane corresponding to the new position of the focus, repeating the acquiring and reconstructing steps, wherein the baseline thermographic MR image is used for thermographic image reconstruction in a subsequent reconstructing step.

10 Claims, 3 Drawing Sheets

(56) References Cited

U.S. PATENT DOCUMENTS

| | | | |
|---|---|---|---|
| 6,128,522 A | 10/2000 | Acker et al. | |
| 6,522,142 B1* | 2/2003 | Freundlich | 324/315 |
| 6,618,620 B1 | 9/2003 | Freundlich et al. | |
| 7,771,418 B2* | 8/2010 | Chopra et al. | 606/28 |
| 7,871,406 B2* | 1/2011 | Nields et al. | 606/27 |
| 8,155,416 B2* | 4/2012 | Nields et al. | 382/131 |
| 8,229,544 B2* | 7/2012 | Tseng et al. | 600/412 |
| 8,235,901 B2* | 8/2012 | Schmidt et al. | 600/439 |
| 8,251,908 B2* | 8/2012 | Vortman et al. | 600/439 |
| RE43,901 E* | 1/2013 | Freundlich et al. | 606/27 |
| 8,409,099 B2* | 4/2013 | Vitek et al. | 600/459 |
| 8,548,561 B2* | 10/2013 | Vortman et al. | 600/407 |
| 8,608,672 B2* | 12/2013 | Vortman et al. | 601/2 |
| 8,641,622 B2* | 2/2014 | Barthe et al. | 600/439 |
| 8,655,430 B2* | 2/2014 | Chou et al. | 600/417 |
| 2003/0236443 A1* | 12/2003 | Cespedes et al. | 600/29 |
| 2005/0065429 A1* | 3/2005 | Zhou | 600/412 |
| 2006/0206105 A1* | 9/2006 | Chopra et al. | 606/27 |
| 2007/0239062 A1* | 10/2007 | Chopra et al. | 600/549 |
| 2008/0146912 A1* | 6/2008 | Richard et al. | 600/411 |
| 2008/0275331 A1* | 11/2008 | Tseng et al. | 600/411 |
| 2009/0171185 A1* | 7/2009 | Chou et al. | 600/411 |
| 2009/0196480 A1* | 8/2009 | Nields et al. | 382/132 |
| 2010/0172567 A1* | 7/2010 | Prokoski | 382/132 |
| 2011/0034833 A1* | 2/2011 | Chopra et al. | 601/3 |
| 2012/0070058 A1 | 3/2012 | Raju et al. | |

OTHER PUBLICATIONS

Cheng et al., "Tissue Thermal Conductivity by Magnetic Resonance Thermometry and Focused Ultrasound Heating" Journal of Magnetic Resonance Imaging, 2002, vol. 16 No. 5, pp. 598-609.

* cited by examiner

MR IMAGING GUIDED THERAPY

FIELD OF THE INVENTION

The invention relates to the field of magnetic resonance (MR) imaging. It concerns a therapeutic system comprising a MR imaging unit and a thermal treatment unit for the focused deposition of thermal energy within tissue of a body of a patient. Moreover, the invention relates to a computer program and to a method of monitoring a therapeutic thermal treatment.

BACKGROUND OF THE INVENTION

As described more detailed herein below, thermal energy deposition is increasingly used in medicine as a means of necrosing diseased tissues. The present invention is disclosed in the following in the context of therapeutic thermal treatment by high intensity focused ultrasound (HIFU). In HIFU a phased array of piezoelectric transducers is used for generating a focused ultrasound beam. It has to be noted, however, that the technique of the invention can be applied equally well in connection with any type of device for the targeted deposition of thermal energy. Examples are lasers or radio frequency antennas.

A therapeutic system comprising an ultrasound therapy unit and a MR imaging unit is generally known, e.g., from WO 2008/152542 A2. In the known system, the MR imaging unit is used to monitor hyperthermia treatments by the ultrasound therapy unit.

Ultrasound is becoming more and more a desirable approach for specific therapeutic interventions. In particular, the use of high intensity focused ultrasound is currently being used as an approach for thermal therapeutic intervention for uterine fibroids and has been examined for possible uses in the treatment of liver, brain, prostate, and other cancerous lesions. Ultrasound has also been the subject of much research as a means for mediating clot dissolution (sono-thrombolysis), and has been shown to increase the efficacy of existing medical treatments such as the use of tPA for stroke patients. Ultrasound mediated drug delivery and gene therapy is a further active area of research. Genetic expression of proteins in gene therapy, and increased delivery of drugs in site-targeted therapies have potential to treat a wide variety of diseases with minimal side-effects. Another application for ultrasound therapy is non-invasive treatment for cosmetic means, e.g., removal of fat. The use of ultrasound in all of these applications is desirable because it allows the non-invasive treatment of deep tissues with little or no effect on overlying organs.

In ultrasound therapy for tissue ablation a tissue of interest is insonified with high intensity ultrasound that is absorbed and converted into heat, raising the temperature of the tissue. As the temperature rises above 55° degrees centigrade, coagulative necrosis of the tissue occurs resulting in immediate cell death. The transducers used in therapy can be outside the body or be inserted into the body e.g. through blood vessels, urethra, rectum etc.

MR thermometry, based on the proton resonance frequency shift (PRFS) in water, is presently considered the 'gold standard' for the non-invasive monitoring of ablative thermal therapies. The temperature dependence of the proton resonance frequency is primarily due to temperature-induced rupture, stretching, or bending of the hydrogen bonds in water. The temperature dependence of pure water is 0.0107 ppm per degree centigrade, and the temperature dependence of water-based tissues is close to this value. Because of a non-homogeneous magnetic field within the MR imaging apparatus used, absolute proton resonance frequency measurements are not possible. Instead, changes in the proton resonance frequency are measured by first taking a MR image before the delivery of heat, and subtracting this base line thermographic image from subsequent measurements. The temperature-induced changes in the proton resonance frequency are estimated by measuring changes in phase of the MR signal, or frequency shift, by means of appropriate and per se known MR imaging sequences.

Problems arise in applications in which the ultrasound transducer is moved to apply therapy at different locations. The motion of the transducer induces variations in the local magnetic field. The phase images before and after the movement cannot be subtracted to calculate the temperature values. One way to avoid this problem is to wait a sufficiently long time after each motion of the ultrasound transducer in order to allow the tissue to cool down to the baseline value (e.g. 37 degrees centigrade) before further treatment. Then a new baseline thermographic MR image can be collected before sonication begins at the new position and/or orientation of the ultrasound transducer. The drawback of this scheme is that the duration of the treatment is much longer than would actually be necessary.

The presently used MR thermometry sequences do not allow the acquisition of volumetric temperature information in three-dimensional space and for different instances in time. Instead, MR thermometry is presently limited to two-dimensional image planes, thereby enabling reasonable temporal update periods for monitoring the treatment. The location of the image planes for MR thermometry must be carefully chosen. This is because safety must be ensured so that critical anatomic structures and normal tissues are protected. Moreover, it has to be made sure that the intended region has been sufficiently heated and the tissue is completely ablated. In applications in which the ultrasound transducer needs to be moved and treatment has to continue with no interruptions between the sonications, as it is the case, e.g. in intracavitary applications, in which rotational movements of the transducer occur, the image planes for MR thermometry need to be continuously moved an updated. Since the therapy involves a plurality of ultrasound transducer positions and orientations, the image planes used for temperature monitoring cannot be chosen to be present corresponding to all relevant positions and orientations of the transducer.

SUMMARY OF THE INVENTION

From the foregoing it is readily appreciated that there is a need for an improved therapeutic system for MR imaging guided HIFU. It is consequently an object of the invention to enable the continuous monitoring of the temperature during thermal treatment based on MR thermometry even in situations in which the position and orientation of the ultrasound transducer is altered.

In accordance with the invention a therapeutic system is disclosed. The system of the invention comprises:

a MR imaging unit arranged to acquire MR signals from a body of a patient positioned in an examination volume, and a thermal treatment unit for the deposition of thermal energy within tissue of the body. The system of the invention is arranged to perform the steps of:

a) initiating thermal treatment by heating the tissue of the body at the position of a focus within the examination volume, b) selective acquisition of MR signals from a first image plane, the position of the focus of the thermal treatment being located within the first image plane,
c) reconstruction of a thermographic MR image from the MR signals acquired from the first image plane,
d) computing a baseline thermographic MR image from the temperature distribution within at least one second image plane being different from the first image plane,
e) moving the focus of the thermal treatment to a new position within the examination volume,
f) changing the position and/or orientation of the first image plane corresponding to the new position of the focus of the thermal treatment,
g) repeating steps b) and c), wherein the baseline thermographic MR image computed in step d) is used for thermographic image reconstruction in subsequent step c).

The invention provides the ability to continuously obtain MR thermometry data in the regions required for therapy monitoring. The invention uses a sparse set of temperature data collected in only a few two-dimensional image planes. The approach of the invention allows the position and orientation of the image plane used for temperature monitoring to follow the transducer without having to wait for the tissue to cool down to the baseline level. Moreover, the invention overcomes problems arising from local magnetic field changes due to the transducer movement.

Although aimed primarily for intracavitary applications, the invention can also be used in other applications in which the applicator used for thermal treatment is moved to various locations and orientations and treatment needs to progress without delays between the therapy steps at the different positions and orientations.

Usually a set of MR images is acquired before the actual treatment begins for planning the therapy. After these planning steps, the thermal treatment is initiated and the heating of the tissue to be treated begins. According to the invention, temperature monitoring on the basis of MR thermometry is performed during treatment from a first (dynamic) region, i.e. the first image plane, which moves in correspondence with the motion of the ultrasound transducer. Moreover, a second (static) region, i.e. the at least one second image plane, is defined which stays fixed for the entire duration of the therapy. During the treatment, temperature information is obtained at substantially regular time intervals in the first and second regions of the body. When the ultrasound transducer is moved this results in a corresponding motion of the focus of the thermal treatment to a new position within the examination volume. The position and/or the orientation of the first region, i.e. the first image plane from which MR thermographic images are continuously acquired and reconstructed, is changed corresponding to the new position of the focus of the thermal treatment. The temperature distribution within the static second region, which has been monitored before the change of the focus of the thermal treatment, is now used to derive the temperature distribution within the changed first region, i.e. after the motion of the focus of the thermal treatment. This is done by computing a baseline thermographic MR image from the temperature distribution collected within the second region and by using this baseline thermographic MR image in subsequent image reconstruction steps. The result is that temperature maps can be produced and displayed to the user of the therapeutic system for image regions that have not been chosen in advance via the user interface of the system. The whole procedure can be repeated several times for subsequent positions and/or orientations of the ultrasound transducer, wherein the first image region is continuously updated.

In accordance with a preferred embodiment of the invention, the baseline thermographic MR image used for subsequent image reconstruction after a change of the focus of the thermal treatment is computed from MR signals that are selectively acquired from the previously chosen static second image region prior to moving the focus of the thermal treatment. In this way a sparse set of temperature data is collected continuously during treatment, thereby enabling temperature monitoring in regions which have not been pre-chosen by the user.

According to a further preferred embodiment of the invention, the first image region is congruent with the second image region after changing the position and/or orientation of the first image region corresponding to the new position of the focus of the thermal treatment. In this embodiment the first image plane is aligned such that the focus of a first treatment is located within the first plane, while the focus of a subsequent second treatment is located within the second plane. The MR signals acquired from the second plane during the first treatment provide a baseline thermographic MR image at the focus of the second treatment, thereby enabling continuous temperature monitoring after the focus has moved from the site of the first treatment to the site of the second treatment. This involves a corresponding planning, wherein several second image planes are chosen in accordance with the sequence of treatment sites.

According to yet a further preferred embodiment of the invention, a set of two or more second image planes is employed which are oriented essentially perpendicular to the first image plane. The baseline thermographic MR images used for image reconstruction steps subsequent to a change of the position and/or orientation of the focus of the treatment may in this case be computed by spatial interpolation of thermographic MR images reconstructed from MR signals acquired from the set of second image planes.

By means of the system of the invention described thus far a method of monitoring a thermal treatment of body tissue can be carried out, the method including:
selective acquisition of MR signals from a first region of the body,
reconstruction of a thermographic MR image from the MR signals acquired from the first region;
computing a baseline thermographic MR image from the spatial temperature distribution within a second region of the body;
changing the position and/or orientation of the first region,
selective acquisition of MR signals from the changed first region,
reconstruction of a thermographic MR image from the MR signals acquired from the changed first region by using the baseline thermographic MR image computed from the spatial temperature distribution within the second region.

The method of the invention can advantageously be carried out in most MR imaging guided HIFU systems in clinical use at present. To this end it is merely necessary to utilize a computer program by which the system is controlled such that it performs the above-explained method steps of the invention. The computer program may be present either on a data carrier (CD, DVD or USB stick) or be present in a data network so as to be downloaded for installation in a corresponding control unit of the therapeutic system.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings FIG. 1 schematically shows a therapeutic system of the invention.

DETAILED DESCRIPTION OF EMBODIMENTS

Figure 1:
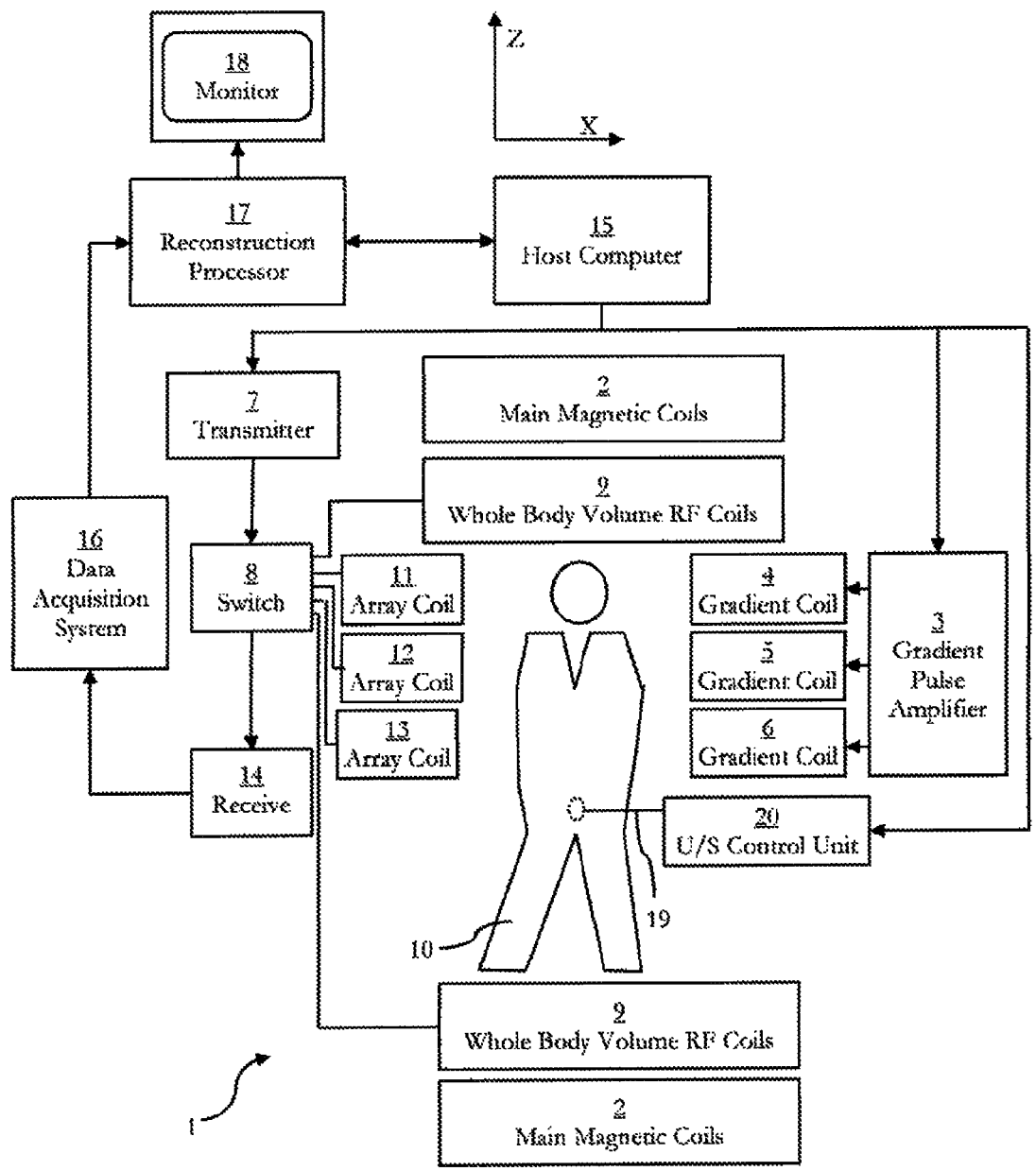

With reference to FIG. 1, a therapeutic system 1 is shown. The system comprises superconducting or resistive main magnet coils 2 such that a substantially uniform, temporally constant main magnetic field is created along a z-axis through an examination volume A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a whole-body volume RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the whole-body volume RF coil 9.

For generation of MR images of limited regions of the body 10, for example by means of parallel imaging, a set of local array RF coils 11, 12, 13 are placed contiguous to the region selected for imaging. The array coils 11, 12, 13 can be used to receive MR signals induced by body-coil RF transmissions.

The resultant MR signals are picked up by the whole body volume RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the gradient pulse amplifier 3 and the transmitter 7 to generate any of a plurality of MR imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

The system 1 further includes a thermal treatment unit comprising a transurethral applicator 19 connected to an ultrasound control unit 20. The ultrasound control unit 20 includes driving electronics as well as motors to move the transducer of the applicator 19. The ultrasound control unit 20 is connected to the host computer 15 of the system. The host computer 15 initiates the thermal treatment and controls the motion of the ultrasound transducer of the applicator 19. The transducer is placed in the urethra of the body 10 with a superior-inferior orientation relative to the patient and radiates the ultrasound energy outward towards the periphery of the prostate. In this way, heating in a single longitudinal plane parallel to the transducer body is provided. To ablate the entire prostate, the transducer is rotated by means of the ultrasound control unit 20 in angular increments.

Figure 2:
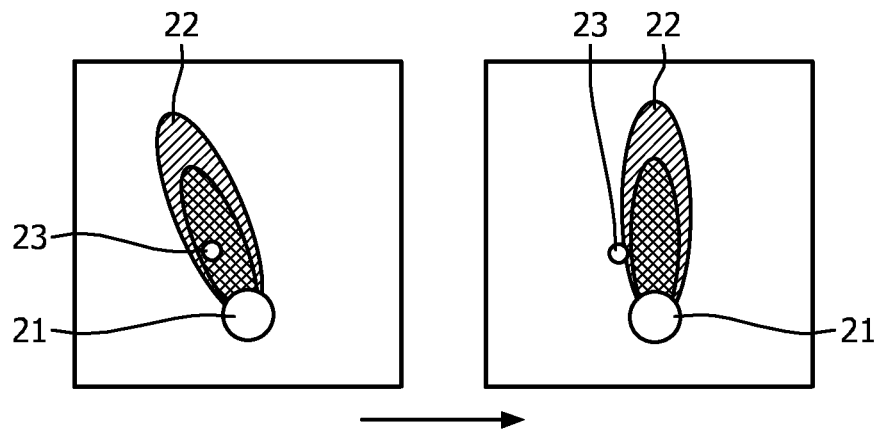
FIG. 2 illustrates a rotational movement of a transurethral ultrasound transducer.

With reference to FIG. 2, MR thermometry images in one image plane transversely oriented with respect to urethra 21 are shown for two different angular orientations of the ultrasound transducer. The temperature and thermal dose profiles 22 reflect the different orientations of the transducer.

Figure 3:
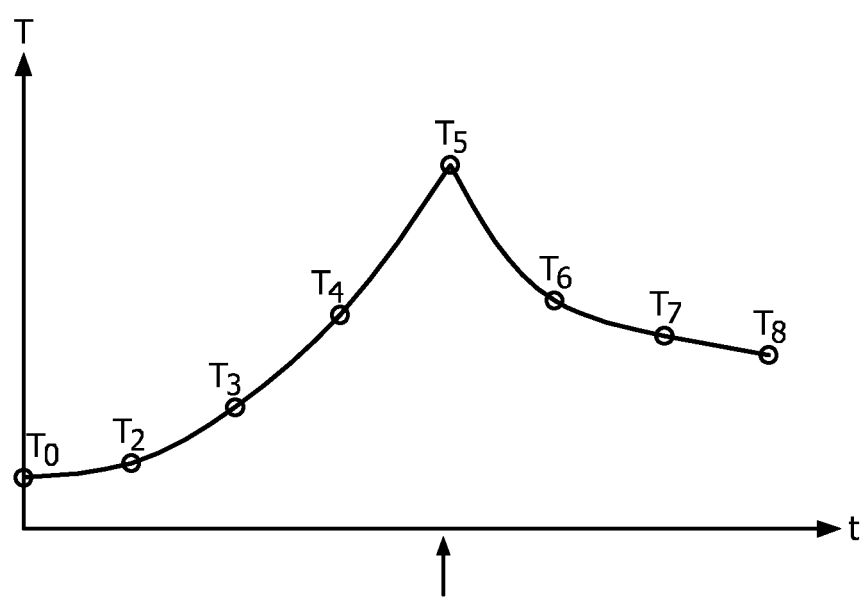
FIG. 3 shows a diagram with temperature values as a function of time at a location depicted in FIG. 2.

With continuing reference to FIG. 2 and with further reference to FIG. 3, the temperature at a point 23 at various time points that are typically about one second or more apart is shown in the diagram of FIG. 3. During the heating phase, the MR thermometry imaging provides temperature differentials at each time point. The temperature values $T_0$ to $T_8$ are computed from the measured phase shift between successive MR images. For the computation of temperature value $T_0$ a corresponding baseline temperature value (e.g. 37 degree centigrade) is assumed.

Shortly after the acquisition of temperature value $T_5$, the transducer is rotated. The corresponding instant is indicated by the arrow in FIG. 3. From this moment on, the temperature at point 23 starts cooling as shown by the drop of the successive temperature values $T_5$, $T_6$, $T_7$, $T_8$. Due to the transducer motion, the MR thermometry based temperature change from temperature value $T_5$ to $T_6$ would not be accurate, since the magnetic field is altered to the point that the phase changes of the MR signals are not representative of the temperature change. The inability to measure the temperature value $T_6$ is problematic since that implies that all temperature values after $T_5$ cannot be measured.

The different orientations of the transducer (as determined by the motor control of the ultrasound control unit 20) are communicated to the host computer 15 of the system 1 (see FIG. 1). The host computer 15 refers to the acoustic intensity profile in the plane at the new orientation of the transducer. Based on the acoustic intensity distribution at the new orientation and the temperature distribution at the time before the rotation of the transducer, a bioheat modeling using the finite difference method can be applied to compute the temperature distribution immediately after the rotation of the transducer. A simpler alternative is to employ a look up table for temperature changes at point 23 obtained through prior bioheat modeling or through phantom experiments. These techniques enable the MR based temperature monitoring process to continue immediately after rotation of the transducer in accordance with the invention. It is not necessary to allow the tissue to cool to the baseline temperature value before further sonications. The thermal dose depends on the entire temperature history and hence the invention enables the accurate computation of the thermal dose beyond the instant at which the transducer is rotated.

Bioheat thermal simulations are widely used in HIFU applications. These simulations can be run a priori using nominal values of tissue properties and the results can be stored as look up tables for each point in space. On the other hand, the simulations can be run on the day of treatment based on the knowledge of the temperature rises in the tissue of the patient from a test run prior to the actual treatment. Moreover, the simulations can be based on the temperature rise at the first orientation of the transducer before the first rotation. Alternatively, the temperature values can be obtained through phantom, ex vivo, or prior in vivo studies. The tissue acoustic and thermal properties for use in the simulations can be estimated in situ using MR thermometry based non-invasive thermal and acoustic parameter estimation approaches (see Cheng et al., "Tissue thermal conductivity by magnetic resonance thermometry and focused ultrasound heating", Journal of Magnetic Resonance Imaging, 2002, vol. 16 (5), pages 598-609). In this way, the temperature distribution within the treated tissue region can be obtained in accordance with the invention. On this basis, the position and/or orientation of the image plane can be changed corresponding to a change of the focus of the thermal treatment without interruption of the treatment and monitoring procedure.

Figure 4:
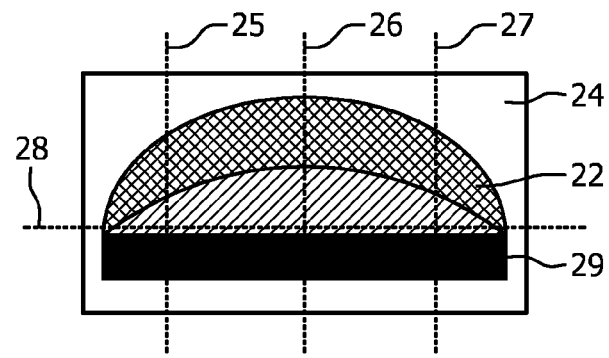
FIG. 4 schematically illustrates a longitudinal thermographic MR image of the prostate.
Figure 5:
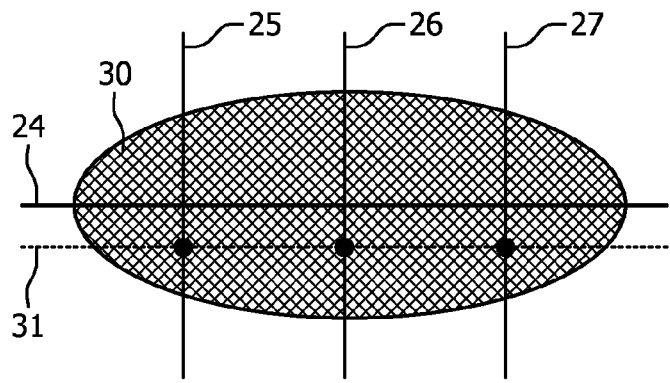
FIG. 5 schematically shows the spatial locations of image planes in accordance with the invention.
Figure 6:
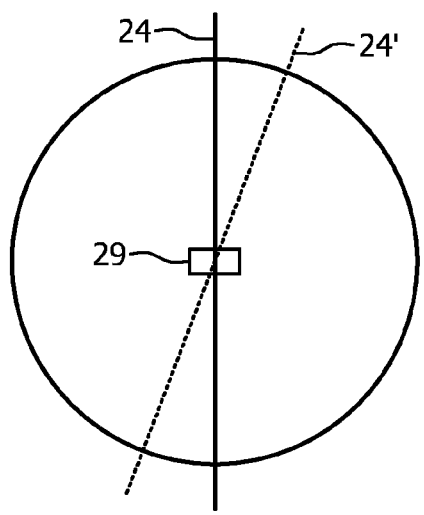
FIG. 6 illustrates the change of an image plane after rotation of the ultrasound transducer.

With reference to FIGS. 4 to 6 it is described in the following how spatially adequate temperature information is made available through the use of static and dynamic temperature monitoring image planes in accordance with the invention. A possible configuration of temperature imaging planes is illustrated in FIG. 4. FIG. 4 shows five image planes 24, 25, 26, 27, 28 that are located around the heating zone of the transducer 29 which is represented as an overlay in the longitudinal image plane 24. The temperature profile 22 in the image plane 24 is shown. The longitudinal plane 24 constitutes the first image plane within the meaning of the invention. It passes through the transducer 29 along the urethra and covers the plane in which the acoustic energy is maximum for the respective orientation of the transducer. When the transducer 29 is rotated, the longitudinal plane 24 will be continuously updated to stay oriented along the maximum of the acoustic energy. The three image planes 25, 26, 27 constitute second image planes within the meaning of the invention. The transverse image planes 25, 26, 27 are static. Their position and orientation is not changed during therapy. A fifth image plane 28 is used for safety assessment. MR thermometry in plane 28 ensures that the near field region of the ultrasound beam is not being excessively heated resulting in unintended effects, such like cavitation, boiling and increased attenuation that can preclude the ultrasound beam from propagating to the far field region. Other potential locations for a safety assessment include the rectal wall and the neurovascular bundles that must be preserved from thermal damage.

The temperature data measured in the sparse set of second image planes 25, 26, 27 is spatially interpolated to obtain temperature estimates in additional image planes which are not directly measured. In this way, a baseline thermographic MR image at the position and orientation of the updated first image plane 24 can be computed before heating commences at the new orientation of the ultrasound transducer 29. This concept is illustrated in FIG. 5, in which a schematic coronal section of the prostate 30 is shown. The solid lines represent the first and second image planes 24, 25, 26, 27, while the dotted line 31 represents the interpolated baseline thermographic MR image at the updated position. The interpolated baseline thermographic MR image is obtained from the measured second image planes 25, 26, 27. The interpolation can be performed by means of any suitable technique, such as linear or spline based interpolation. This enables the longitudinal temperature imaging plane, i.e. the first image plane, to stay always parallel to the sonication plane without interruption of thermal therapy and temperature monitoring.

FIG. 6 illustrates the rotation of the first image plane. The orientation of the first image plane before rotation of the transducer 29 is designated by 24. The orientation after rotation of the transducer 29 is designated by 24'. The temperature map in the rotated first image plane 24' is obtained in accordance with the invention from continuous temperature measurements in the static transverse second image planes 25, 26, 27 as shown in FIG. 5. In this way, plane 24 is constantly updated to follow the orientation of the transducer 29.

In another (not depicted) embodiment, two different longitudinal planes are chosen as first and second image planes within the meaning of the invention. The image planes are aligned such that the first image plane is always located at the site of the focus of the thermal treatment, while the other (second) image plane is located at the site of the next treatment. The temperature measurement in the second image plane provides baseline temperature values that can be used in order to enable continued temperature monitoring when the focus of the thermal treatment is moved from the first site to the second site.

The invention claimed is:

1. Therapeutic system (1) comprising:
a MR imaging unit arranged to acquire MR signals from a body (10) of a patient positioned in an examination volume,
a thermal treatment unit (19, 20) for depositing thermal energy within tissue of the body (10),
wherein the system is arranged to perform the steps of:
a) initiating thermal treatment by heating the tissue of the body (10) at a position of a focus within the examination volume,
b) selectively acquiring MR signals from a first image plane (24), the position of the focus being located within the first image plane (24),
c) reconstruction of a thermographic MR image from the MR signals acquired from the first image plane (24),
d) computing a baseline thermographic MR image from a temperature distribution within at least one second image plane (25, 26, 27) being different from the first image plane (24),
e) moving the focus of the thermal treatment to a new position within the examination volume,
f) changing the position and/or orientation of the first image plane (24) corresponding to the new position of the focus of the thermal treatment,
g) repeating steps b) and c), wherein the baseline thermographic MR image computed in step d) is used for thermographic image reconstruction in subsequent step c).

2. System of claim 1, further being arranged to compute the baseline thermographic MR image in step d) from MR signals selectively acquired from the at least one second image plane (25, 26, 27).

3. System of claim 1, wherein the first image plane (24) is congruent with the second image plane (25, 26, 27) after changing the position and/or orientation in step f).

4. System of claim 1, wherein the second image plane (25, 26, 27) is oriented essentially perpendicular to the first image plane (24).

5. System of claim 1, further being arranged to acquire MR signals from a set of two or more second image planes (25, 26, 27), the baseline thermographic MR image being computed in step d) by spatial interpolation of thermographic MR images reconstructed from the MR signals acquired from the set of second image planes (25, 26, 27).

6. System of claim 1, further being arranged to repeat steps b) to f) several times, the baseline thermographic MR image computed during each repetition in step d) being used for thermographic image reconstruction in step c) of the respective subsequent repetition.

7. System of claim 6, wherein the position and/or orientation of the at least one second image plane (25, 26, 27) remains fixed during repetitions of steps b) to f).

8. System of claim 1, further being arranged to reconstruct the thermographic images from the local proton resonance frequency shift.

9. Computer program product comprising a non-transitory storage medium comprising computer readable instructions executable by a computer for:
   initiating thermal treatment by heating the tissue of a body,
   selective acquisition of MR signals from a first region of the body,
   reconstruction of a thermographic MR image from the MR signals acquired from the first region based on a first baseline thermographic image,
   computing a second baseline thermographic MR image from a spatial temperature distribution within a second region of the body,
   changing the position and/or orientation of the first region,
   selective acquisition of MR signals from the changed first region,
   reconstruction of a thermographic MR image from the MR signals acquired from the changed first region by using the second baseline thermographic MR image.

10. Method of monitoring a thermal treatment of body tissue, including:
   selective acquisition of MR signals from a first region of a body,
   reconstruction of a thermographic MR image from the MR signals acquired from the first region based on a first baseline thermographic image;
   computing a second baseline thermographic MR image from a spatial temperature distribution within a second region of the body;
   changing the position and/or orientation of the first region,
   selective acquisition of MR signals from the changed first region,
   reconstruction of a thermographic MR image from the MR signals acquired from the changed first region by using the second baseline thermographic MR image.

* * * * *